United States Patent
Gau

(10) Patent No.: US 9,535,032 B2
(45) Date of Patent: Jan. 3, 2017

(54) CARTRIDGE FOR LIQUID TRANSPORT

(71) Applicant: GeneFluidics, Inc., Irwindale, CA (US)

(72) Inventor: Jen-Jr Gau, Pasadena, CA (US)

(73) Assignee: GeneFluidics, Inc., Irwindale, CA (US)

( * ) Notice: Subject to any disclaimer, the term of this patent is extended or adjusted under 35 U.S.C. 154(b) by 712 days.

(21) Appl. No.: 13/913,328

(22) Filed: Jun. 7, 2013

(65) Prior Publication Data

US 2014/0027313 A1 Jan. 30, 2014

Related U.S. Application Data

(60) Provisional application No. 61/741,805, filed on Jul. 27, 2012.

(51) Int. Cl.
*G01N 27/417* (2006.01)
*G01N 27/416* (2006.01)
*G01N 27/327* (2006.01)

(52) U.S. Cl.
CPC ........ *G01N 27/416* (2013.01); *G01N 27/3277* (2013.01); *Y10T 29/49124* (2015.01)

(58) Field of Classification Search
None
See application file for complete search history.

(56) References Cited

U.S. PATENT DOCUMENTS

| | | | | |
|---|---|---|---|---|
| 6,300,141 B1 * | 10/2001 | Segal | ............... | G01N 33/54366 204/228.1 |
| 2005/0196855 A1 | 9/2005 | Gau et al. | | |
| 2007/0053796 A1 | 3/2007 | Gau et al. | | |
| 2009/0011952 A1 | 1/2009 | Gau et al. | | |
| 2010/0108539 A1 * | 5/2010 | Iwanaga | .......... | G01N 33/54366 205/687 |
| 2011/0201099 A1 | 8/2011 | Anderson et al. | | |
| 2011/0220656 A1 | 9/2011 | Gau | | |
| 2013/0143221 A1 * | 6/2013 | Beauchemin | ........ | G01N 27/416 435/6.12 |

OTHER PUBLICATIONS

Copenheaver, Blaine R., International Search Report and Written Opinion, PCT/US2013/044835, International Searching Authority, United States Patent and Trademark Office, Jan. 17, 2014.
Wittmann-Regis, Agnes, International Preliminary Report on Patentability and Written Opinion, PCT/US2013/044835, The International Bureau of WIPO, Feb. 9, 2015.

* cited by examiner

*Primary Examiner* — J. Christopher Ball
(74) *Attorney, Agent, or Firm* — Gavrilovich, Dodd & Lindsey, LLP

(57) ABSTRACT

The cartridge includes a sensor structure that has multiple sensors positioned on a substrate. The cartridge also includes a common channel defined in the substrate such that a fluid flowing in the common channel contacts each of the sensors as a result of the fluid flowing from an inlet of the common channel to an outlet of the common channel.

19 Claims, 10 Drawing Sheets

CARTRIDGE FOR LIQUID TRANSPORT

RELATED APPLICATIONS

This Application claims the benefit of U.S. Provisional Patent Application Ser. No. 61/741,805, filed on Jul. 27, 2012, entitled "Cartridge for Liquid Transport" and incorporated herein in its entirety.

FIELD

The invention relates to liquid transport systems and more particularly to systems for delivery of a liquid to a sensor.

BACKGROUND

A variety of assays can be performed using an assay chip that includes one or more sensors positioned on a substrate. A cartridge can be employed to transport various liquids to the sensors. The cartridge typically includes one or more reservoirs that each holds one of the solutions. During the operation of the cartridge, the cartridge is inserted into a machine that causes the liquids in the reservoirs to be transported to the one or more sensors. The machine can then operate the one or more sensors so as to perform an assay on each of the sensors.

When the sensors are electrochemical sensors, the different liquids are delivered to each of the sensors in order to construct a test probe within a test volume that is positioned on the sensors. The different liquids include different components of the test volume including components of the test probe that bond to one another and/or to the sensor. Since it is desirable to perform different assays on different sensors, it is also desirable for the test probes built on different sensors to be different. As a result, cartridges for transporting the liquids to the sensors often include complex arrangements of channels and valves that introduce complexity, costs and inefficiencies into the system. As a result, there is a need for simplification of the process of performing multiple different assays on a sensor chip.

SUMMARY

A cartridge includes a sensor structure that has multiple sensors positioned on a substrate. The cartridge also includes a common channel defined in the substrate such that a fluid flowing in the common channel contacts each of the sensors as a result of the fluid flowing from an inlet of the common channel to an outlet of the common channel.

In another embodiment of the system, the cartridge includes a channel positioned such that contents of the channel contact one or more sensors in the cartridge. The system also includes a selection valve in liquid communication with reagents that are each in a different container and in liquid communication with the channel in the cartridge. The selection valve is configured to select any one of the reagents for transport from the container that contains the selected reagent into the common channel while preventing transport of the unselected reagents into the common channel.

A method of forming one of the layers of the cartridge can include overlapping substrates with one another such that more than one of the substrates each has an overlapped portion that is overlapped by one or more of the other substrates and also has an exposed portion that is not overlapped by any of the other substrates. The method also includes forming electrodes on the substrates while they are overlapped. The electrodes are formed on the exposed portions of different substrates.

BRIEF DESCRIPTION OF THE FIGURES

FIG. 1A is a bottomview of the sensor structure.

FIG. 1B is a topview of the sensor structure.

FIG. 1C a cross section of the sensor structure shown in FIG. 1A taken along the line labeled C in FIG. 1A.

FIG. 2A is a topview of the channel structure.

FIG. 2B is a bottomview of the channel structure.

FIG. 2C a cross section of the channel structure shown in FIG. 2A taken along the line labeled C in FIG. 2A.

FIG. 2D a cross section of the channel structure shown in FIG. 2A taken along the line labeled D in FIG. 2A.

FIG. 3A is a topview of the base structure.

FIG. 3B is a bottomview of the sensor structure.

FIG. 3C a cross section of the base structure shown in FIG. 3A taken along the line labeled C in FIG. 3A.

FIG. 4A is a topview of the cartridge. FIG. 3B is a bottomview of the sensor structure.

FIG. 4B a cross section of the cartridge taken along the line labeled B in FIG. 4A.

FIG. 4C a cross section of the cartridge taken along the line labeled C in FIG. 4A.

FIG. 5A is a topview of the assembled cartridge where dashed lines are used to show features that underlie the top of the cartridge.

FIG. 5B is a topview of the base structure.

FIG. 5C is a cross section of the cartridge shown in FIG. 5A taken along the line that is labeled C in FIG. 5A.

FIG. 5D is a cross section of the cartridge shown in FIG. 5A taken along the line that is labeled D in FIG. 5A.

DESCRIPTION

Figure 1A:
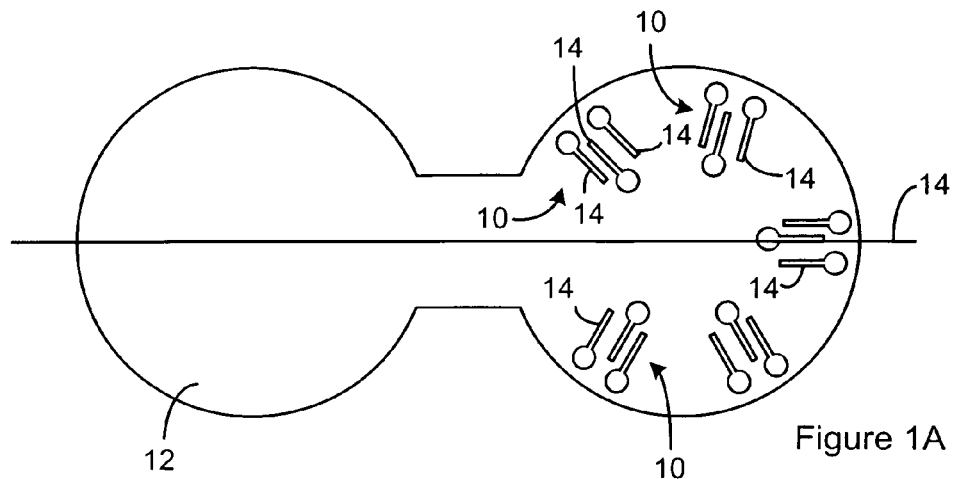
FIG. 1A through FIG. 1C illustrate a sensor structure for the cartridge.

In some instances, the cartridge includes multiple sensors positioned on a substrate. Suitable sensors include, but are not limited to, electrochemical sensors. The cartridge also includes a common channel that guides liquids from an inlet to an outlet. The common channel and sensors are arranged such that the liquids guided through the common channel come into contact with each of the sensors.

The cartridge can be included in a system that includes a selection valve. The selection valve is in liquid communication with several reservoirs. Each of the reservoirs includes a different reagent. The selection valve is also in liquid communication with the common channel. The system also includes a pump configured to pump liquid from the selection valve into the common channel. The selection valve can select any one of the reagents by opening a liquid pathway from the reservoir that contains the selected reagent to the pump while closing liquid pathways between the other reservoirs and the pump. The system can operate the pump so as to transport the selected reagent through the common channel and into contact with the sensors. As a result, the system can select a series of reagents to be transported to the sensors by selecting and pumping different reagents in a sequence that transports the desired sequence of reagents into contact with the sensors.

The sequence of reagents transported to the sensors is selected to properly prepare the sensors. For instance, when the sensors are electrochemical sensors, the sequence of reagents transported to the sensors is selected to prepare test probes and/or test volumes in contact with the sensors. After the formation of the test volumes, electrochemical sensors can be operated so as to perform an electrochemical analysis such as cyclic voltammetry.

The test volumes contacting different sensors can be different. For instance, a preliminary portion of the test volumes on different sensors can be prepared before assembly of the cartridge. The preliminary portion of the test volume can be different for different sensors. Different sensors having different preliminary portions can result in the formation of different test volumes on different sensors. As a result, the analysis performed by different sensors can test for the presence and/or amount of different target components. The use of a common channel in combination with a selection valve to prepare the different test volumes greatly reduces the complexity associated with the design and operation of the cartridges.

Additionally, the above cartridge can be associated with reduced fabrication complexity. For instance, the cartridge can be constructed of multiple layers. One of the layers can be a sensor structure that includes the sensors mounted on a substrate. In some instances, these sensors include multiple electrodes positioned on the substrate. Because this substrate can perform functions in the cartridge other than supporting electrodes, the electrodes may occupy a fraction of the space available on the substrate. As a result, during the fabrication of the sensors, the substrates can be overlapped during while electrodes are applied to the substrates. This ability to overlap the substrates during fabrication of the sensor structures allows multiple sensor structures to be fabricated concurrently and accordingly provides a more efficient fabrication process.

Figure 1B:
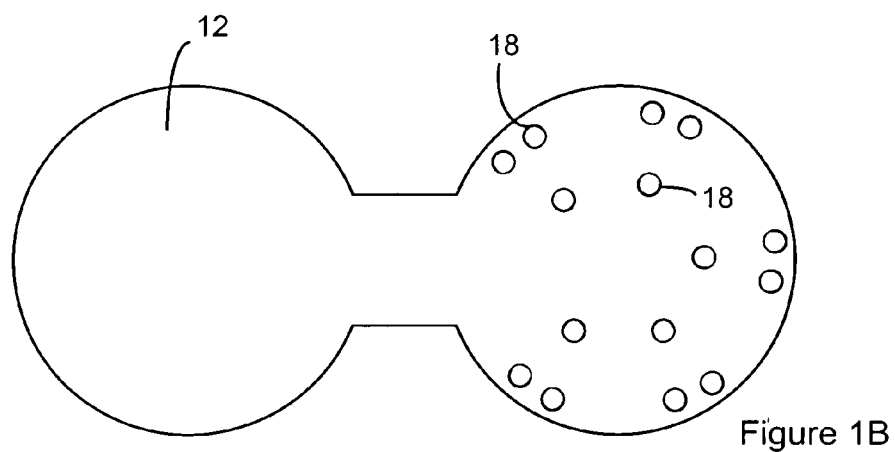
Figure 1C:
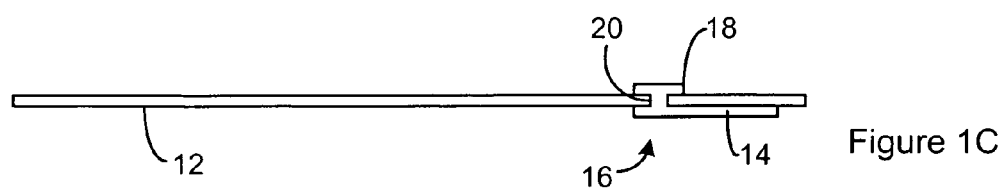

FIG. 1A through FIG. 1C illustrate a sensor structure for the cartridge. FIG. 1A is a bottomview of the sensor structure. FIG. 1B is a topview of the sensor structure. FIG. 1C a cross section of the sensor structure shown in FIG. 1A taken along the line labeled C in FIG. 1A. The sensor structure includes one or more sensors 10 on a substrate 12. Suitable sensors 10 include, but are not limited to, electrochemical sensors, impedance sensors, and electrochemiluminescence sensors. In a preferred example, the sensor 10 is an electrochemical sensor. An electrochemical sensor employs electrical energy to cause a chemical reaction in a liquid in contact with the sensor. The chemical reaction changes the chemical composition of a component in the liquid into another composition. For instance, the reaction changes one or more compounds or elements in the liquid into another compound or element. The reactions caused by electrochemical sensors are typically redox reactions where electrons from an electrode within the sensor are exchanged with a component in the liquid. When the one or more sensors are electrochemical sensors, the sensors can be used in electrochemical analysis techniques that include, but are not limited to, cyclic voltammetry.

Each of the sensors includes a plurality of electrodes 14 positioned on the substrate 12. Suitable materials for the substrate 12 include, but are not limited to, acrylics, polyesters (PET), polyethylene-terephthalate glycol (PETG), polycarbonates, thermoplastics, glass, Poly(methyl methacrylate) (PMMA), Cyclic Olefin Copolymer (COC). A suitable thickness for the substrate 12 of the sensor structure includes, but is not limited to, a thickness greater than 10 μm, 1 mm, or 5 mm and/or less than 1 inch, 5 cm, or 1 mm. Although the substrate 12 is shown as being constructed from a single material, the substrate 12 can have a composite construction.

The electrodes 14 in the illustrated sensor include a working electrode between a reference electrode and a counter electrode. In some instances, each of the electrodes 14, including the reference electrode, is formed from a single layer of an electrically conductive material. Suitable electrically conductive materials, include, but are not limited to, gold. Electrical leads 16 provide electrical communication between each of the electrodes 14 and an electrical contact 18. As is evident from FIG. 1C, the electrical leads can extend through vias 20 formed in the substrate 12. The use of vias allows the sensors and the electrical contacts to be positioned on opposing sides of the substrate 12. As a result, electronics (not shown) can be connected to the electrical contacts from the side of the sensor structure that is opposite the sensors.

The sensor structure of FIG. 1A through FIG. 1C can be fabricated using traditional integrated-circuit fabrication techniques. Other sensor constructions are disclosed in U.S. patent application Ser. No. 09/848,727, filed on May 5, 2001, entitled "Biological Identification System with Integrated Sensor Chip and incorporated herein in its entirety.

During operation of one of the sensors to analyze a test volume for the presence and/or amount of a target component, the sensors are each in electrical communication with electronics (not shown) configured to apply a potential between the working electrode and the reference electrode of a sensor while monitoring current passing through a circuit that includes the working electrode, a liquid sample positioned on the sensor, and the counter electrode. When the sensor is employed as an electrochemical sensor, the potential applied between the working electrode and the reference electrode can be raised to a level that can cause electron transfer to occur between the working electrode and a component in the sample. The electron transfer allows current to flow through the circuit that includes the working electrode, the sample and the counter electrode. As a result, the sensor can be employed in electrochemical analysis such as voltammetry including cyclic voltammetry. Operation of the sensor so as to detect the presence of an agent is discussed in more detail in U.S. patent application Ser. No. 09/848,727, filed on May 3, 2001, entitled "Biological Identification System with integrated Sensor Chip" and incorporated herein in its entirety.

The sensor structure need not include sensors but can include electrodes that provide other functions. For instance, the sensor structure can include one or more electrokinetic devices on the substrate 12. Suitable electrokinetic devices includes electrophoretic devices. These devices can include two or more electrodes positioned on the substrate 12. The electronics can form an electrical field between the electrodes so as to cause movement of compounds and/or components within the sample. A sensor structure that includes one or more electrokinetic devices need not include any sensors or can include the one or more electrokinetic devices in addition to one or more sensors. In other instances, the sensor structure includes electrodes arranged to provide mixing of liquids or culturing of antibiotics.

Figure 2A:
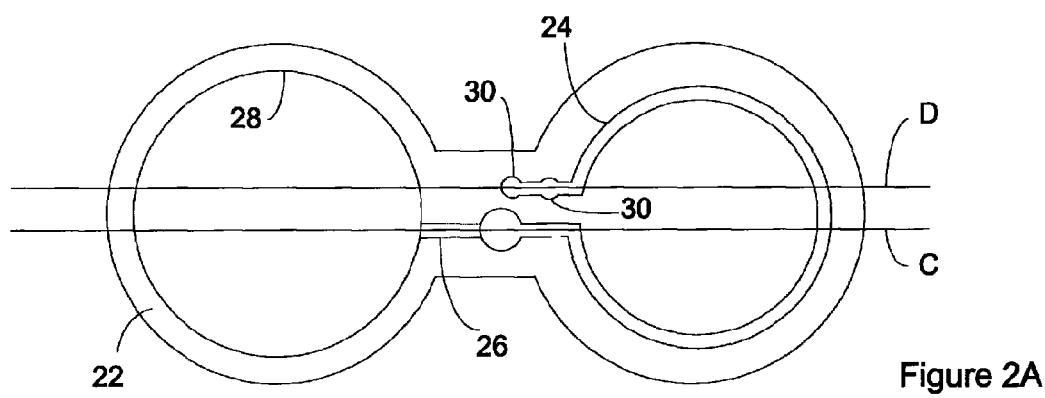
FIG. 2A through FIG. 2D illustrate a channel structure.
Figure 2B:
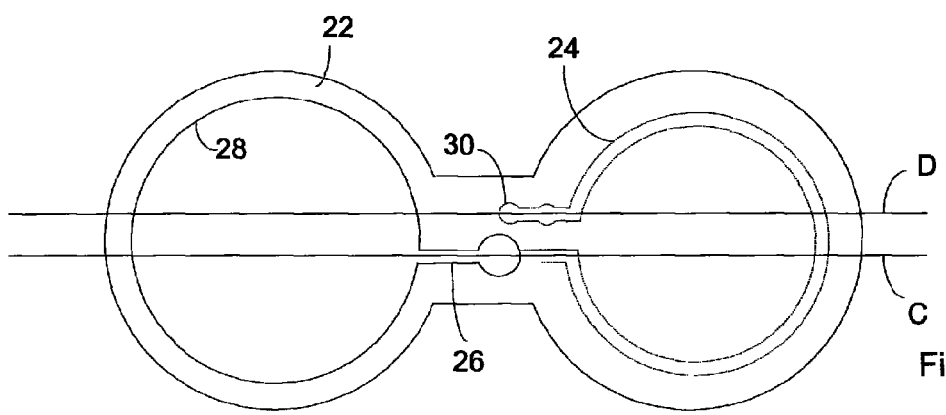
Figure 2C:
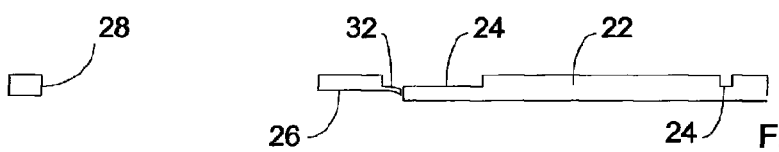
Figure 2D:
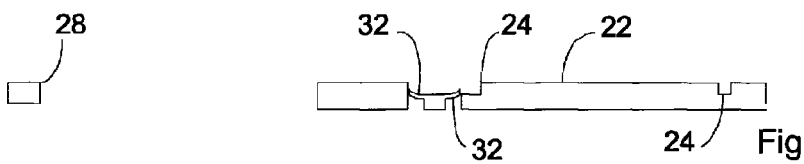

FIG. 2A through FIG. 2D illustrate a channel structure. FIG. 2A is a topview of the channel structure. FIG. 2B is a bottomview of the channel structure. FIG. 2C a cross section of the channel structure shown in FIG. 2A taken along the line labeled C in FIG. 2A. FIG. 2D a cross section of the channel structure shown in FIG. 2A taken along the line labeled D in FIG. 2A. In FIG. 2A and FIG. 2B, dashed lines illustrate features located on the opposing side of the substrate from the features shown in solid lines.

The channel structure includes recesses that extend part way into a substrate 22 so as to define channels and/or reservoirs within the cartridge. The recesses are formed in both sides of the substrate 22. For instance, a common channel recess 24 extends into the top of the substrate 22 while a waste channel recess 26 extends into the bottom of the substrate 22. One or more of the recesses can extend through the substrate 22. For instance, a waste reservoir recess 28 extends through the substrate 22. As will become evident below, the common channel recess 24 defines a portion of the common channel in the cartridge and the waste channel recess 26 defines a portion of a waste channel in the cartridge. Additionally, the waste reservoir recess 28 defines a portion of a waste reservoir in the cartridge.

The common channel recess 24 includes expanded regions 30. As will become evident below, these expanded regions 30 serve as inlet ports through which reagents, samples, and/or other liquids can be introduced into the common channel 44.

The portion of the common channel recess 24 that defines the bottom of the common channel recess 24 includes a flap 32. Additionally, the portion of the waste reservoir recess 28 that defines the bottom of the waste reservoir recess 28 includes a flap 32. The flaps 32 serve as check valves during the operation of the cartridge. For the purposes of illustration, the flaps 32 are shown in the open position where liquid is allowed to flow past the flaps 32.

Suitable materials for the substrate 22 of the channel structure include, but are not limited to, thermal plastic elastomer (TPE), Urethane Elastomer, silicone and synthetic polymer. A suitable thickness for the substrate 22 of the channel structure includes, but is not limited to, a thickness greater than 10 $\mu$m, 10 mm, or 1 inch and/or less than 3 inches, 1 cm, or 100 $\mu$m. Although the substrate 22 is shown as being constructed from a single material, the substrate 22 can have a composite construction.

Figure 3A:
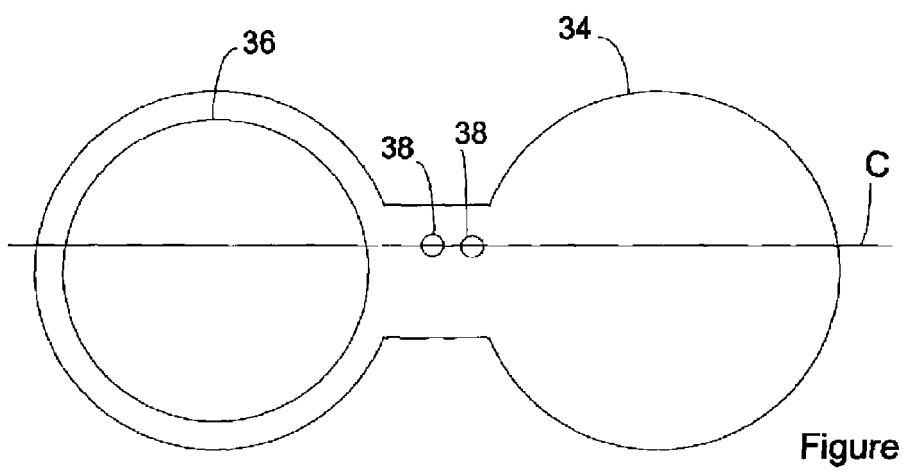
FIG. 3A through FIG. 3C illustrate a base structure.
Figure 3B:
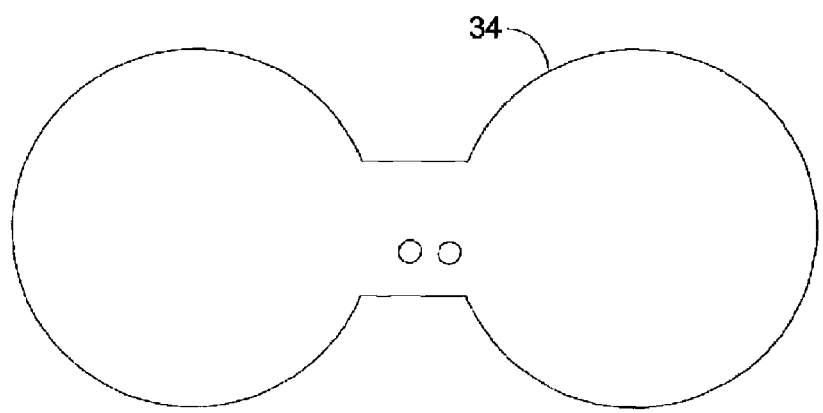
Figure 3C:
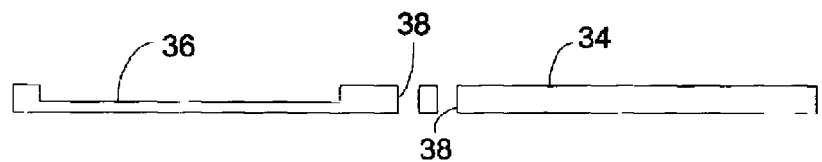

FIG. 3A through FIG. 3C illustrate a base structure. FIG. 3A is a topview of the base structure. FIG. 3B is a bottomview of the sensor structure. FIG. 3C a cross section of the base structure shown in FIG. 3A taken along the line labeled C in FIG. 3A.

The base structure includes recesses that extend part way into a substrate 34 so as to define channels and/or reservoirs within the cartridge. For instance, a waste recess 36 extends into the top of the substrate 34. One or more of the recesses can extend through the substrate 34. For instance, inlet port recesses 38 extend through the substrate 34. As will become evident below, the waste recess 36 defines a portion of a waste reservoir in the cartridge. Additionally, the inlet port recesses 38 each defines a portion of an inlet port 46 in the cartridge.

Suitable materials for the substrate 34 of the base structure include, but are not limited to, acrylics, polyesters (PET), polyethylene-terephthalate glycol (PETG), polycarbonates, thermoplastics, glass, Poly(methyl methacrylate) (PMMA), Cyclic Olefin Copolymer (COC). A suitable thickness for the substrate 34 of the base structure includes, but is not limited to, a thickness greater than 1 mm, 5 cm, or 1 inch and/or less than 5 inches, 10 cm, or 5 mm. Although the substrate 34 is shown as being constructed from a single material, the substrate 34 can have a composite construction.

Figure 4A:
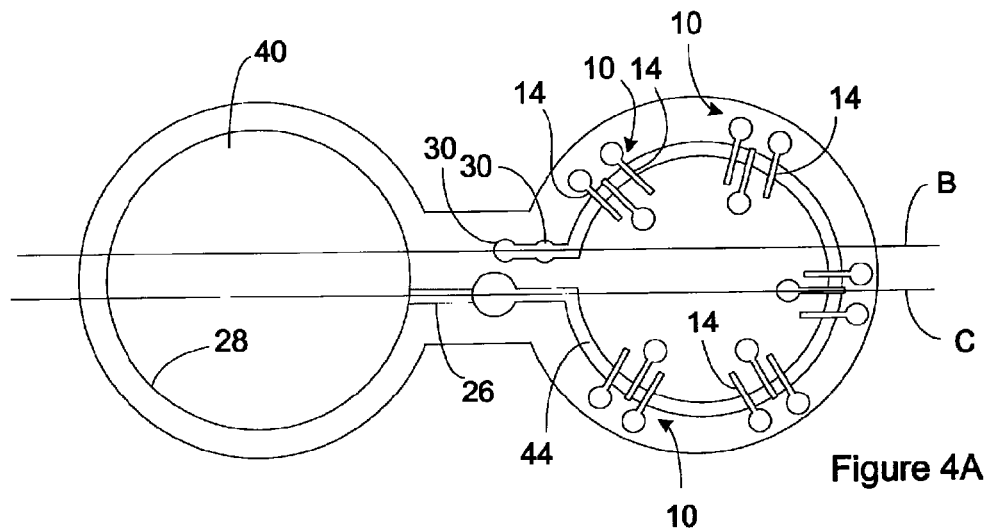
FIG. 4A through FIG. 4C illustrate a cartridge assembled from the sensor structure of FIG. 1A through FIG. 1C, the channel structure of FIG. 2A through FIG. 2D, and the base structure of FIG. 3A through FIG. 3C.
Figure 4B:
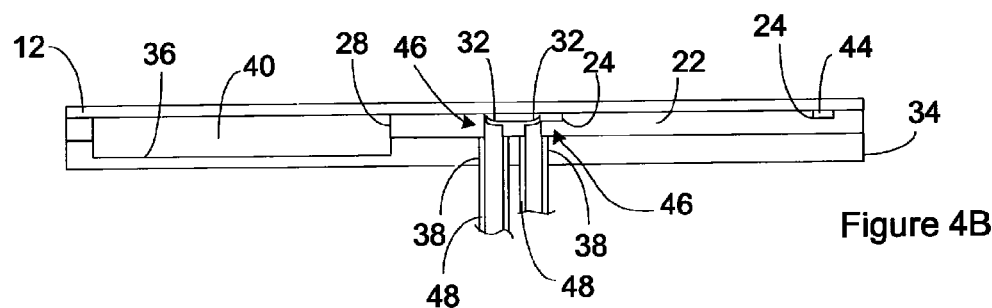
Figure 4C:
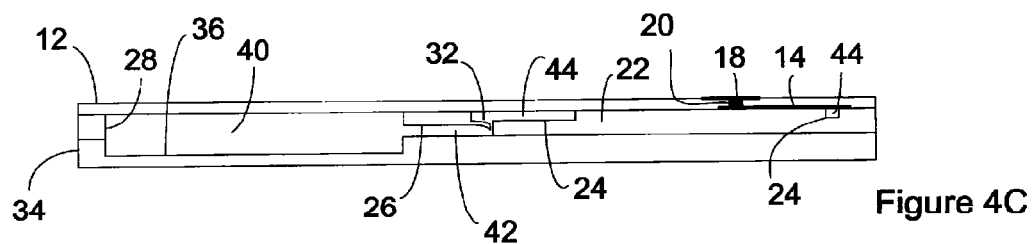

FIG. 4A through FIG. 4C illustrate a cartridge assembled from the sensor structure of FIG. 1A through FIG. 1C, the channel structure of FIG. 2A through FIG. 2D, and the base structure of FIG. 3A through FIG. 3C. FIG. 4A is a topview of the cartridge. FIG. 3B is a bottomview of the sensor structure. FIG. 4B a cross section of the cartridge taken along the line labeled B in FIG. 4A. FIG. 4C a cross section of the cartridge taken along the line labeled C in FIG. 4A. The substrate 12 in the sensor structure of FIG. 4A is treated as transparent. As a result, features in the layers of the cartridge that underlie the sensor structure are visible in FIG. 4A. Additionally, the electrical contacts 18 are not shown in FIG. 4A in order to prevent confusion between the electrical contacts and other features.

The cartridge includes the channel structure between the sensor structure and the base structure. In some instances, the channel structure is immobilized relative to the sensor structure and the base structure using an adhesive, glue, epoxy, heat bonding, push pin clamping, ultrasonic welding, insert molding or solvent bonding. The dimensions and shape of the substrate 12 of the sensor structure, the substrate 22 of the channel structure, and the substrate 34 of the base structure can be matched. As a result, the edges of the sensor structure, channel structure, and base structure can be aligned.

As is evident from FIG. 4B and FIG. 4C, the waste reservoir recess 28 and the waste recess 36 align so as to form a waste reservoir 40 in the cartridge. The waste channel recess 26 and the base structure form a waste channel 42 in the cartridge. The waste channel 42 is open to the waste reservoir 40 so the contents of the waste channel 42 can flow into the waste reservoir 40.

The common channel recess 24 and the sensor structure form a common channel 44 through the cartridge. The common channel recess 24 is aligned with the electrodes 14 such that at least a portion of each electrode is positioned within the common channel 44. As a result, the contents of the common channel 44 come into contact with each of the electrodes 14.

The flap 32 in the waste reservoir recess 28 forms a check valve positioned at an interface between the common channel 44 and the waste channel 42. The check valve is constructed to open when liquid flows from the common channel 44 into the waste channel 42 but close when liquid attempts to flow the other direction. As a result, the check valve reduces or stops flow of liquid into the common channel 44 from the waster reservoir. Accordingly, the check valve can serve as the outlet for the common channel 44.

The expanded regions 30 of the common channel recess 24 each aligns with one of the inlet port recesses 38 to form an inlet port 46 in the cartridge. As shown in FIG. 4B, a fluid conduit such as a needle 48 with a lumen can be inserted into the inlet port 46. The flaps 32 in the common channel 44 each forms a check valve in the common channel 44. The check valve are constructed to open when liquid flows from one of the fluid conduits into the common channel 44 but closes when liquid attempts to flow out of the common channel 44 into the fluid conduit. As a result, these check valves reduce or stop flow of liquid from the common channel 44 into the liquid conduits and serve as an inlet to the common channel 44.

Figure 5A:
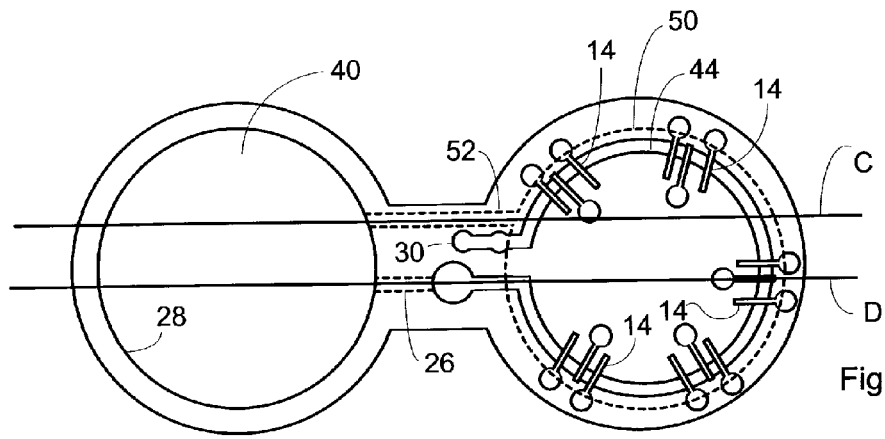
FIG. 5A through FIG. 5D illustrate a cartridge having a channels structure between a sensor structure and a base structure.
Figure 5B:
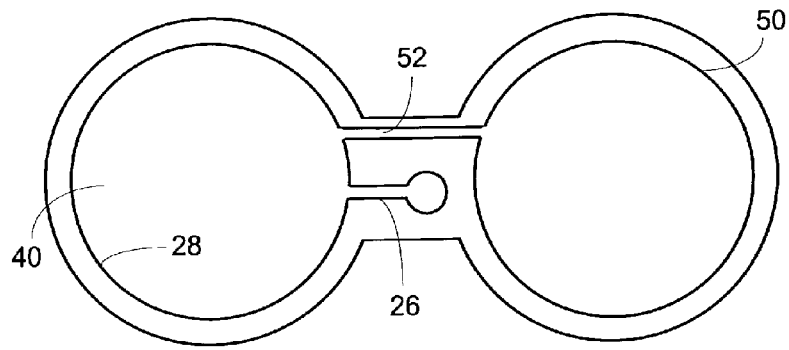
Figure 5C:
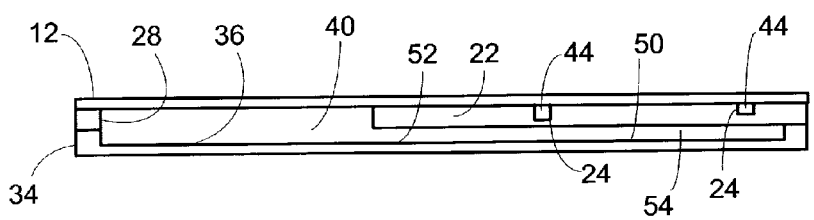
Figure 5D:
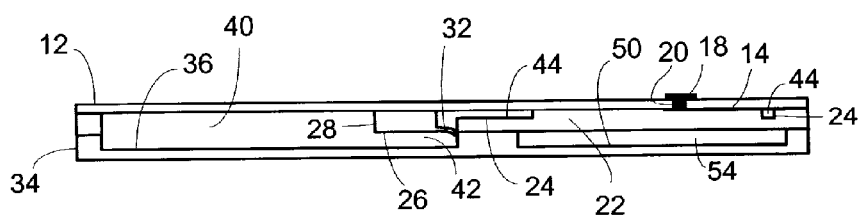

The recesses that define one or more channels can extend into layers other than the channel layer as shown by FIG. 5A through FIG. 5D. FIG. 5A is a topview of the assembled cartridge where dashed lines are used to show features that underlie the top of the cartridge. FIG. 5B is a topview of the base structure. FIG. 5C is a cross section of the cartridge shown in FIG. 5A taken along the line that is labeled C in FIG. 5A. FIG. 5D is a cross section of the cartridge shown in FIG. 5A taken along the line that is labeled D in FIG. 5A. The substrate 12 in the sensor structure of FIG. 5A is treated as transparent. As a result, features in the layers of the cartridge that underlie the sensor structure are visible in FIG. 5A. Additionally, the electrical contacts 18 are not shown in FIG. 5A in order to prevent confusion between the electrical contacts and other features.

The waste channel recess 26 extends into the top of the substrate 34 of the base structure rather than into the bottom of the substrate 22 of the channel structure. As is evident from FIG. 5D, the waste channel 42 is defined by the portion of the waste channel recess 26 extending into the top of the base structure in combination with the bottom of the channel structure.

The base structure also includes a secondary waste recess 50 and a secondary waste channel recess 52 that each extends part way into the substrate 34 of the base structure. The secondary waste recess 50 and the channel structure define a secondary waste reservoir 54 within the cartridge. The secondary waste channel recess 52 and the channel structure define a secondary waste channel that provides a liquid pathway between the waste reservoir 40 and the secondary waste reservoir 54.

In the cartridge of FIG. 5A through FIG. 5D, the recesses can all be etched from one side of the substrate 22 of the channel structure because recesses do not extend into both sides. Accordingly, the cartridge of FIG. 5A through FIG. 5D may be associated with a simplified fabrication process.

When the sensors are electrochemical sensors, the sensors generally must be prepared before an electrochemical analysis is performed. For instance, a test volume is formed on each of the sensors. The test volume is generally prepared by applying a series of different liquids to one or more electrodes in each of the sensors. In some instances, the series of liquids are applied so as to construct a particular compound on the one or more electrodes in each of the sensors. One version of preparing the test volume includes forming a test probe that is bonded to a reporter and an adhesions layer as disclosed in U.S. patent application Ser. No. 12/154,971, filed on May 28, 2008, entitled "Chip Assay Having Improved Efficiency," and incorporated herein in its entirety. The adhesion layer is bonded to at least one electrode of each sensor such that the adhesion layer is between the electrode and the test probe. Accordingly, the adhesion layer provides adhesion between the electrode and the test probe. A homogeneous or heterogeneous self-assembly monolayer can serve as the adhesion layer. In some instances, a suitable self-assembly monolayer includes active probes with streptavidin bonded to DAD-C12-SH (12-mercapto(8-biotinamide-3,6-dioxaoctyl)dodecanamide) and 11-mercapto-1-undecanol as spacers The electrode to which the adhesion layer is bonded includes the working electrode and may also include the reference electrode and/or the counter electrode of each sensor.

The reporter is bonded to the test probe such that the test probe is between the adhesion layer and the reporter. The test probe includes the target component that is being sought by the electrochemical analysis. For instance, the test probe can include the target component between a capture probe and a signaling probe with the capture probe being bonded to the adhesion layer. The adhesion layer has a higher affinity for the capture probe than the working electrode has for the capture probe. Accordingly, the adhesion layer can serve to bond the capture probe to the working electrode. The capture probe serves to link the electrode(s) to the target component. Suitable capture probes include, but are not limited to, deoxyribonucleic acids (DNA), ribonucleic acids (RNA), peptide nucleic acids (PNA), locked nucleic acids (LNA) and proteins such as antibodies. The electrochemical analysis can indicates the presence and/or amount of the target component. Suitable target components include, but are not limited to, polysaccharides, nucleic acids, cells and strands of genetic materials such as DNA or RNA and antibodies.

Other test probes can be used in conjunction with the sensors. For instance, the test probe can also be adapted for detecting the presence of a cell or a protein. For instance, the capture probe can be the primary antibody of a sandwich assay and the signaling probe can be the secondary antibody of the sandwich assay. Suitable target components for a sandwich assay include, but are not limited to, proteins, polysaccharides and nucleic acids having binding sites specific to the antibody or cells with proteins having binding sites specific to the antibody. A suitable reporter for use with a test probe for detecting a cell or protein includes, but is not limited to, Horseradish Peroxidase (HRP), AP (alkaline phosphotase) and glucose peroxidase. In addition to the test probe and adhesion layer, the sample volume can include other components such as mediators. Additional details regarding the operation of the sensor, test volume contents and generation, and test probe assembly can be found in U.S. patent application Ser. No. 12/154,971, which is incorporated herein in its entirety.

In order to assemble the test volume, the one or more sensors are exposed to a series of reagents as described in U.S. patent application Ser. No. 12/154,971. Each of the different reagents can include one or more components of the test volume such as one or more components of the adhesion layer, test probe and reporter that are to bond to the electrode and/or to other components that are already bonded to the electrode. For instance, a reagent can include a sample that includes the target component, another reagent can include the signaling probe, and another reagent can include the reporter. Reagents can also include other components of the test volume. For instance, another reagent can include a mediator. The reagents can include one or more wash solutions that are applied to the sensors before, between, or after the application of other reagents to the sensors. The wash solution can remove any unbound components or non-specifically bound components from the sensors while leaving specifically bound components on the sensors. As a result, the application of one or more wash solutions can decrease the amount of noise present in the electrochemical analysis. In general, specifically bound components include covalent bonds to other components or an electrode on the sensor while non-specifically bound components are bonded to other components or an electrode on the sensor by weaker bonds such as hydrogen bonds.

Figure 6A:
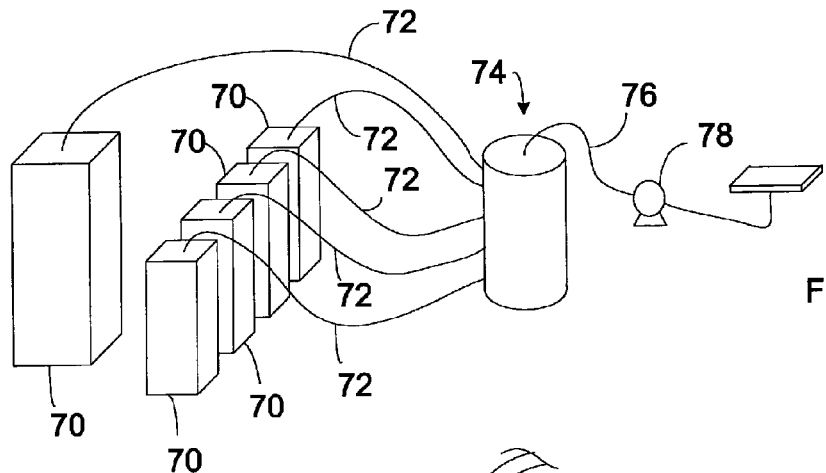
FIG. 6A illustrates a system for applying a series of liquids to the sensors in a cartridge.

FIG. 6A illustrates a system for applying the series of liquids to the sensors in the cartridge. Each of the different liquids is contained in a container 70. An input conduit 72 connects each of the different containers 70 to a selection valve 74. Suitable input conduits 72 include tubes. An output conduit 76 connects the selection valve 74 to a pump 78. A suitable pump 78 includes, but is not limited to, a peristaltic pump that compresses the output conduit 76. The output conduit 76 is connected to the inlet port 46. For instance, the output conduit 76 can terminate in a device that can be inserted into the inlet port 46 as shown in FIG. 4B. As an example, the output conduit can terminate in a needle 48 that can be inserted into the inlet port 46 as shown in FIG. 4B.

When the selection valve 74 selects a particular one of the liquids, the selection valve 74 opens a continuous liquid pathway from the container 70 that contains the selected liquid to the common channel 44 in the cartridge. As a result, when the pump is operated, the selected liquid is transported from the container 70 into the liquid pathway. If the pump is operated for a sufficient duration, the selected liquid enters the common channel 44.

Figure 6B:
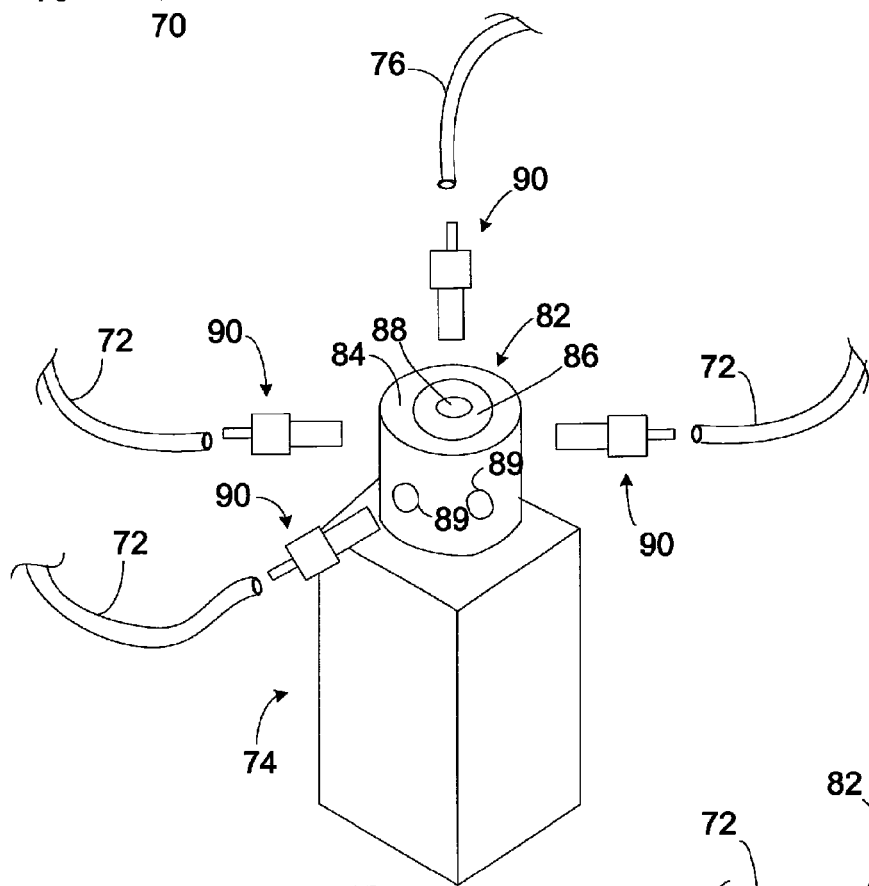
FIG. 6B illustrates an example of a selection valve suitable for use in the system of FIG. 6A.

FIG. 6B illustrates an example of a suitable selection valve 74. The selection valve 74 includes a base that contains a motor (not shown). A distribution device 82 is positioned on the base. The distribution device 82 includes a sleeve 84 mounted on a mandrel 86. An output lumen 88 extends into the mandrel 86. The output lumen 88 is configured to receive an interface device 90 that provides an interface between the mandrel 86 and the output conduit 76. In particular, the interface device 90 provides a liquid pathway from the output conduit 76 into the output lumen 88. Multiple input lumens 89 extend into the sleeve 84. The input lumens 89 are each configured to receive an interface device 90 that each provides an interface between the sleeve 84 and one of the input conduits 72. In particular, the interface device 90 provides a liquid pathway between from an input conduit 72 into one of the input lumens 89.

Figure 6C:
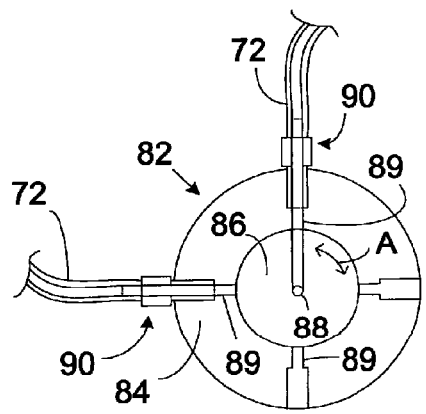
FIG. 6C provides a cross section of the selection valve.

FIG. 6C provides a cross section of the distribution device 82. The cross section is taken through the input lumen 89 shown in FIG. 6B. Although not evident from FIG. 6C, a portion of the output lumen 88 is shown in FIG. 6C; however, the other portion of the output lumen 88 is not illustrated due to the two dimensional nature of FIG. 6C. The unillustrated portion of the output lumen 88 is connected to the illustrated portion of the output lumen 88 and extends upwards through the mandrel 86 to the opening of the output lumen 88 shown in FIG. 6B. Accordingly, the output lumen 88 provides a liquid pathway from the illustrated portion of the output lumen 88 to the opening of the output lumen 88 shown in FIG. 6B.

In FIG. 6C, a cross section of two of the interface devices 90 are shown. Each interface device 90 is inserted into one of the input lumens 89 and also into one of the input conduits 72. A conduit through the interface device 90 completes a liquid pathway from the input conduit 72 into the input lumen 89.

The motor (not shown) in the base is configured to move the sleeve 84 and the mandrel 86 relative to one another as shown by the arrow labeled A in FIG. 6C. For instance, the motor can be configured to rotate the mandrel 86 within the sleeve 84. Valve electronics (not shown) can operate the motor such that the output lumen 88 aligns with one of the input lumens 89 as shown in FIG. 6C. The alignment between an input lumen 89 and the output lumen 88 opens a liquid pathway from the input conduit 72 connected to the aligned input lumen 89 into the output lumen 88 and accordingly into the common channel 44. In contrast, when the output lumen 88 is aligned with one of the input lumens 89, the outside of the mandrel 86 obstructs the other input lumens 89. As a result, there is no liquid pathway from the other input conduits 72 into the output lumen 88. Accordingly, the reagents carried by these input conduits 72 cannot flow into the output lumen 88 and accordingly cannot flow into the common channel 44. As a result, valve electronics (not shown) that operate the selection valve 74 can select a particular liquid from one of the containers 70 by operating the motor such that the output lumen 88 is aligned with the input lumen 89 that is in liquid communication with that particular liquid.

The valve electronics that operate the selection valve 74 can also serve as pump electronics (not shown) that operate the pump. Alternately, the pump electronics can be in addition to the valve electronics. Once the electronics select a particular liquid from one of the containers 70, the pump electronics can operate the pump. Operation of the pump causes the selected liquid (the liquid that is in liquid communication with the aligned input lumen 89) to flow from the container 70, into the output lumen 88, and then into the output conduit 76. If the pump is operated for a sufficient duration, the selected liquid is pumped into the common channel 44, into the waste channel 42, and then into the waste reservoir 40. If the cartridge is constructed according to FIG. 5A and FIG. 5B and the pump is operated for a sufficient duration, the selected liquid can also be pumped into the secondary waste channel and then into the secondary waste reservoir 54.

As noted above, when the one or more sensors in the cartridge are electrochemical sensors, before performing an electrochemical analysis, the sensors are prepared by transporting a series of different liquids into contact with each of the sensors. The liquids include reagents, and the sample to be tested for the presence and/or amount of a target component. The electronics can form the test volume by selecting the first liquid in the series of liquids to be delivered to the sensors and operating the pump until the desired volume of the selected liquid is transported into the output lumen 88 and output conduit 76, the next liquid is then selected and the pump is again operated until the desired volume of the selected liquid is transported into the output lumen 88 and output conduit 76. The sequence can be repeated until the desired number of reagents is transported into the output lumen 88 and the output conduit 76.

Figure 7:
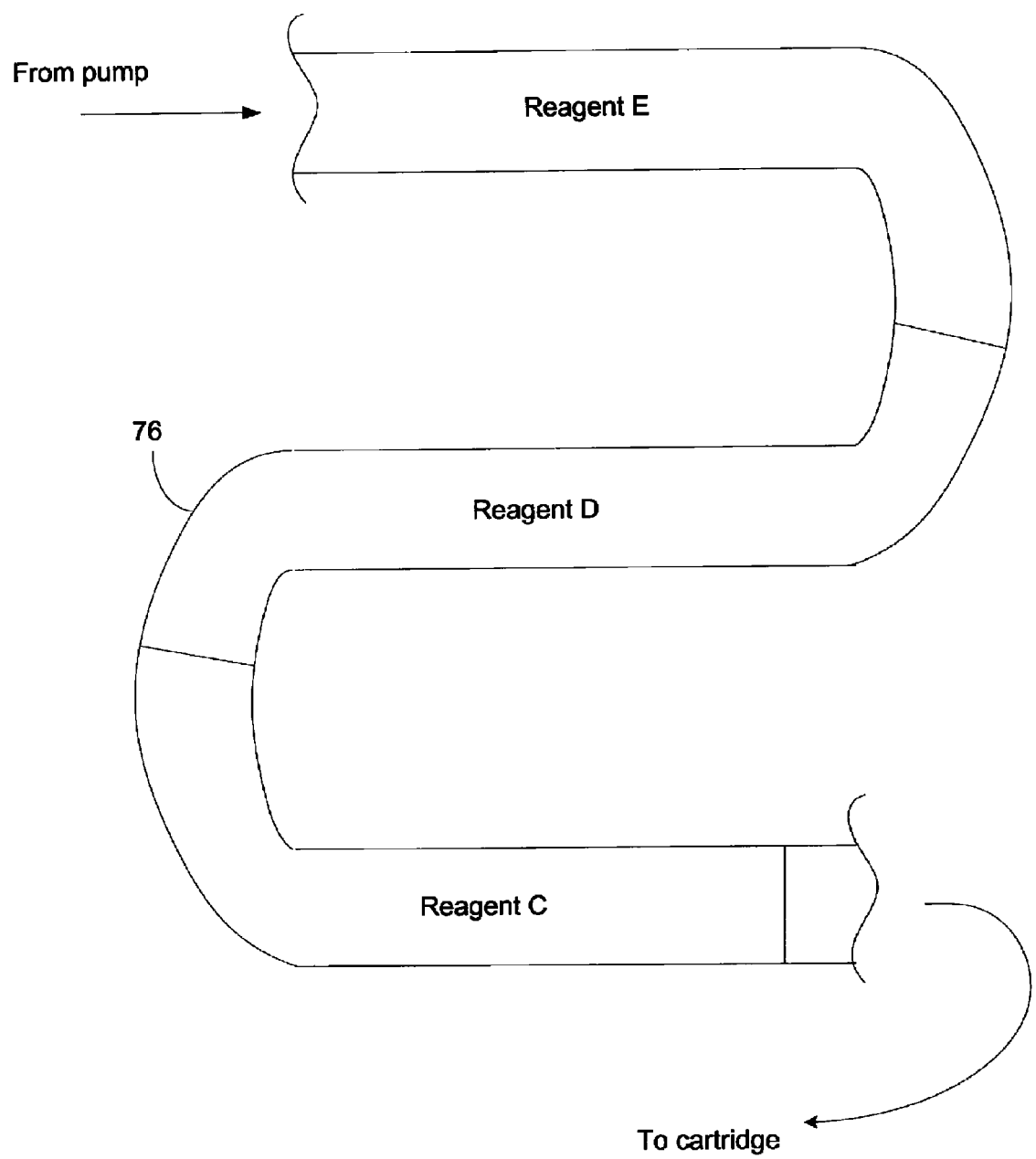
FIG. 7 illustrates multiple reagents loaded into a single conduit.

In some instances, the output conduit 76 has a length that effectively allows the reagents to be stored in the output conduit 76 before being delivered to the cartridge. As illustrated in FIG. 7, the reagents can be loaded into the output conduit 76 in the proper sequence. When it is time to prepare the test volumes, the pump can be operated so that the series of reagents stored in the output conduit 76 is pumped through the common channel 44 and into the waste reservoir 40. Alternately, the output conduit 76 has a length that allows the reagents to be pumped through the common channel 44 while other reagents are being pumped out of their containers 70.

In some instances, the last reagent selected and pumped is a wash solution or dummy solution. When the pump is a peristaltic pump, there should be liquid remaining in the output conduit 76 in order for the pump to retain its ability to pump. In these circumstances, additional liquid remains in the output conduit 76 after delivery of each reagent to the cartridge. The remaining liquid serves as a backing solution. A wash solution or other dummy solution can serve as this backing solution.

One of the liquids transported through the common channel 44 into contact with the sensors is the sample to be tested for the presence and/or amount of a target component. The sample can be placed into one of the containers 70 delivered to the common channel 44 like one of the reagents using the selection valve 74 and pump. Alternately, the sample can be delivered directly into the common channel 44 through one of the inlet ports 46 as shown in FIG. 4B. For instance, the sample can be delivered into one of the ports using a needle 48 such as a hypodermic needle or other device. The sample can be delivered into the common channel 44 before any of the reagents are delivered into the common channel 44. Alternately, the sample can be delivered into the common channel 44 between the delivery of other reagents into the common channel 44 or during the delivery of another reagent into the common channel 44. For instance, the pump electronics can be configured to stop operating the pump between the delivery of certain reagents into the common channel 44 or during the delivery of a reagent into the common channel 44. While the pump is stopped, the sample can be delivered into the common channel 44 and the pump electronics can resume.

Since a series of different reagents flow through the common channel 44, the common channel 44 remains filled with liquid during the operation of the sensors. As a result, the different test volumes are included in a continuous liquid phase during the operation of the sensors. As a result, the sensors are spaced sufficiently far apart so as to avoid both electrical and chemical cross-talk during the operation of the sensors.

In the above cartridge, the common channel 44 is the only channel that carries reagents into contact with the sensors. As a result, the sensors are essentially exposed to the same sequence of reagents. In some instances, the reagents are delivered in a sequence where wash solution is alternated with non-wash reagents. In some instances, the non-wash reagents typically include one or more components that are to be specifically bonded to the electrodes and/or to another component that is already bonded to the electrode. Alternating wash solutions with non-wash reagents can increase the degree of commonality that the different sensors experience during preparation of the test volumes that each contact one of the sensors. For instance, stopping the pump only when a wash solution is being applied can ensure that each sensor is exposed to the non-wash reagents for about the same period of time. Additionally or alternatively, the use of wash solutions between non-wash reagents can reduce or stop intermingling of different reagents. Suitable wash solutions include, but are not limited to, DI water, PBS buffer, Triton buffer, Tris buffer, Tris-buffered saline (TBS), Tween 20 and commercial wash buffers.

Since there is only one channel carrying reagents to each of the different sensors and that channel is common to each of the different sensors, each sensor is exposed to essentially the same sequence of reagents. As a result, the test volume that forms on each sensor can have about the same chemical composition. For instance, the test volume that forms on each of the sensors can include the same compounds or about the same compounds at the same concentrations or about the same concentrations. The variations in the test volumes formed on different sensors may be a result of sensors that are positioned further along the common channel 44 seeing a reduced concentration of certain compounds due to those compounds binding to sensors located earlier in the common channel 44.

In some instances, the test volumes formed on different sensors are substantially different. As noted above, the sensors can include an adhesion layer. The adhesion layer can be formed as a result of delivering the series of reagents to the sensors. Alternately, the adhesion layers can be in place on the sensors before the delivery of the reagents to the sensors. For instance, the adhesion layer can be present on at least the working electrode in each of the sensors before the cartridge is assembled. The adhesion layer on different sensors can be the same. Alternately, the adhesion layer on different sensors can be different. When the adhesion layers on different sensors are different, different test probes will form on different sensors. As a result, the resulting test volumes can also be different.

In addition to using different adhesion layers or as an alternative to using different adhesion layers, the test probes attached to different sensor can be different. For instance, the capture probe(s) on a portion of the sensors can be different from the capture probe(s) on a different portion of the sensors. Since different capture probes will bond to different target components, the use of different capture probes allows a portion of the sensors to test for the presence and/or amount of a different target component than another portion of the sensors. When a portion of the sensors are bonded to a different capture probe than another portion of the sensors, the different capture probes can be in place on the sensors before the delivery of the reagents to the sensors. For instance, the capture probes can be present on at least the working electrode in each of the sensors before the cartridge is assembled. In one example, at least the adhesion layer and the capture probes are bonded to the adhesion layer on each of the sensors before the cartridge is assembled.

The electrochemical analysis performed with each sensor can be the same. When the test volume on each sensor is essentially the same, the results of each electrochemical analysis can then be checked against one another to provide an enhanced degree of reliability of results and/or to reduce false positives. Alternately, the electrochemical analysis performed on different sensors can be different. For instance, the electrochemical analysis performed on a portion of the sensors can be performed over a different range of voltages and/or at a different frequency than another portion of the sensors. When different electrochemical analyses are performed on different test volumes, it is possible to concurrently test for the presence and/or amount of different target components.

Figure 8A:
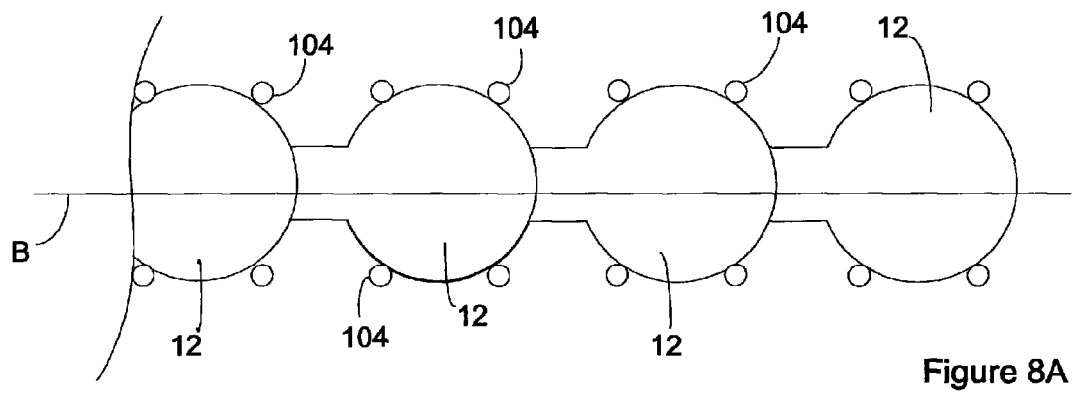
FIG. 8A is a topview of multiple substrates for different sensor structures overlapping one another.
Figure 8B:
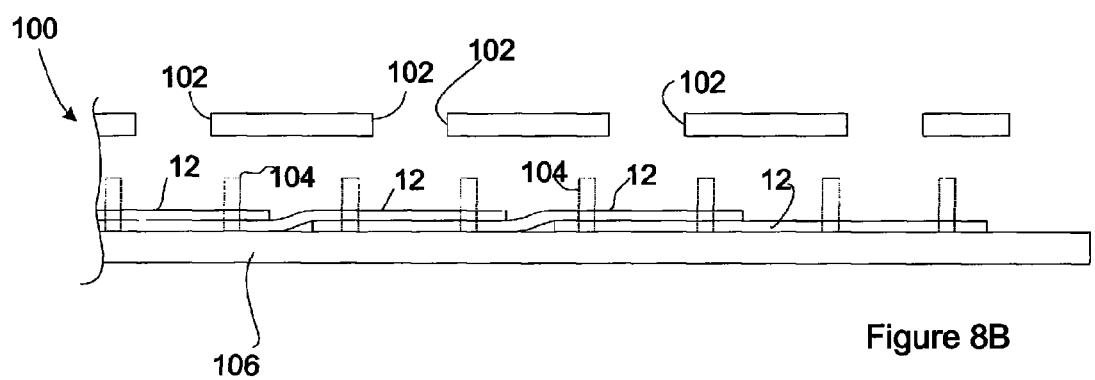
FIG. 8B is a cross section of the sensor structures shown in FIG. 8A taken along the line that is labeled B in FIG. 8A.

The sensor structure is constructed such that different sensor structures can partially overlap one another during the fabrication process. For instance, FIG. 8A is a topview of the substrates 12 for different sensor structures overlapping one another. FIG. 8B is a cross section of the sensor structures shown in FIG. 8A taken along the line that is labeled B in FIG. 8A. Items that are behind the cross section of FIG. 8B are shown as dashed lines. Additionally, a mask 100 is shown in FIG. 8B that is not present in FIG. 8A.

On each of the substrates 12, the exposed region where the electrodes are to be formed are exposed. In contrast, the portion of the substrate 12 that is overlapped by another sensor structure is the portion that excludes electrodes. This arrangement allows the electrodes to be concurrently patterned on the exposed portions of the different substrates 12. A suitable method for patterning the electrodes on the substrates 12 of the overlapping substrates 12 of different sensor structures is illustrated in FIG. 8B. The electrode material can be applied to the substrates 12 through a mask 100. The mask 100 can have openings 102 positioned over the portions of the substrates 12 where the electrodes are to be formed and can protect the regions of the substrates 12 that are exposed and also between the electrodes. A suitable method for applying electrode materials such as metals includes, but is not limited to, sputtering. Sputtering is a process where atoms of the electrode material are ejected from a solid of the electrode material due to bombardment of the solid electrode material by energetic particles such as ions. In general, momentum exchange between the ions and the atoms of the electrode material cause the ejection of the atoms from the solid electrode material. A suitable mask for techniques such as sputtering include a shadow mask. In one example, the electrodes are formed on the substrate 12 of the sensor structure by sputtering through a shadow mask.

Figure 8C:
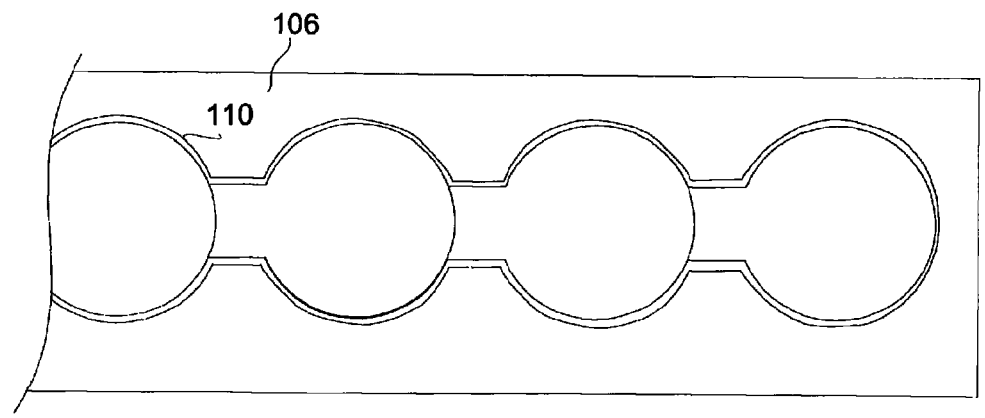
FIG. 8C is a topview of a platform having a recess that receives substrates arranged as shown in FIG. 8A.

The overlapping substrates 12 can be given the proper alignment through the use of alignment structures 104. FIG. 8A and FIG. 8B illustrate alignment structures 104 extending upwards from a platform 106. Suitable alignment structures 104 include, but are not limited to, pins or pegs. The alignment structures 104 are arranged such that when substrate 12 for different sensor structures are positioned within the alignment structures 104, the alignment structures 104 limit the movement of the substrates 12. For instance, the perimeters of the substrates 12 can contact the substrate 12 or be an average of less than 1 µm, 10 µm, or 100 µm from the substrates 12. In some instances, the alignment structures 104 contact the substrate 12 and have an average distance of less than 1 µm, 10 µm, or 100 µm from the substrates 12 and are arranged such that the alignment structures 104 limit movement of the substrates 360° in the plane of the substrates 12. Other alignment structures 104 can be employed. For instance, FIG. 8C is a topview of a platform 106 having a recess 110 that receives the substrates 12. The sides of the recess work as the alignment structures 104. For instance, the sides of the recess contact the substrate 12 or are an average of less than 1 µm, 10 µm, or 100 µm from the substrates 12. As is evident from FIG. 8C, the sides of the recess limit movement of the substrates 12 in 360° in the plane of the substrates 12.

The shapes of the different substrates 12 can also be selected to provide alignment while the substrates 12 overlap one another. For instance, the substrates 12 can be shaped such that the perimeter of the edge of the overlapping substrate 12 is aligned with more than 5%, 25%, 30%, 35%, or even 40% of the perimeter of edge of the underlying substrate 12 even though the overlying substrate 12 leaves at least 5%, 20%, 40%, 50%, 60% or 75% of area of the upper surface of the underlying substrate 12 exposed and/or covers more than 25%, 50% or 75% of the area of the upper surface of the underlying substrate 12. While a variety of shapes can be used to achieve this degree of alignment, these configurations can be achieved when the substrate 12 has a configuration where two flaps are hinged together by a narrow hinge region. In the configurations, the hinge region occupies less than 20%, or 50% of the substrate 12 area. The portion of the perimeter that is aligned can be increased when the perimeter of the two flaps of a substrate 12 have both the same size and shape. Increasing the portion of the perimeters that are aligned assists in achieve the proper alignment between the different substrates 12. An example of a substrate 12 configuration where the two flaps have the same size and shape is illustrated in FIG. 1A. These geometries can also be achieved with other substrate 12 shapes.

Although FIG. 8A and FIG. 8B show the substrates 12 overlapping such that only one substrate 12 is positioned over another substrate 12, it is possible to arrange the substrates 12 such that more than two substrates 12 overlap one another.

In one example, the substrates 12 are each configured such that each substrate 12 includes two flaps that each has the same size and shape and are hinged together; the substrates 12 are arranged such that more than 20%, 50% or 75% of each underlying substrate 12 is exposed; and the substrates 12 are aligned such that the perimeter of the edge of each overlapping substrate 12 is aligned with more than 5%, 20%, or 30% of the perimeter of the edge of each underlying substrate 12. In some instances, the electrodes of one or more electrochemical sensors are patterned on these substrates 12 by sputtering through a shadow mask.

Figure 9A:
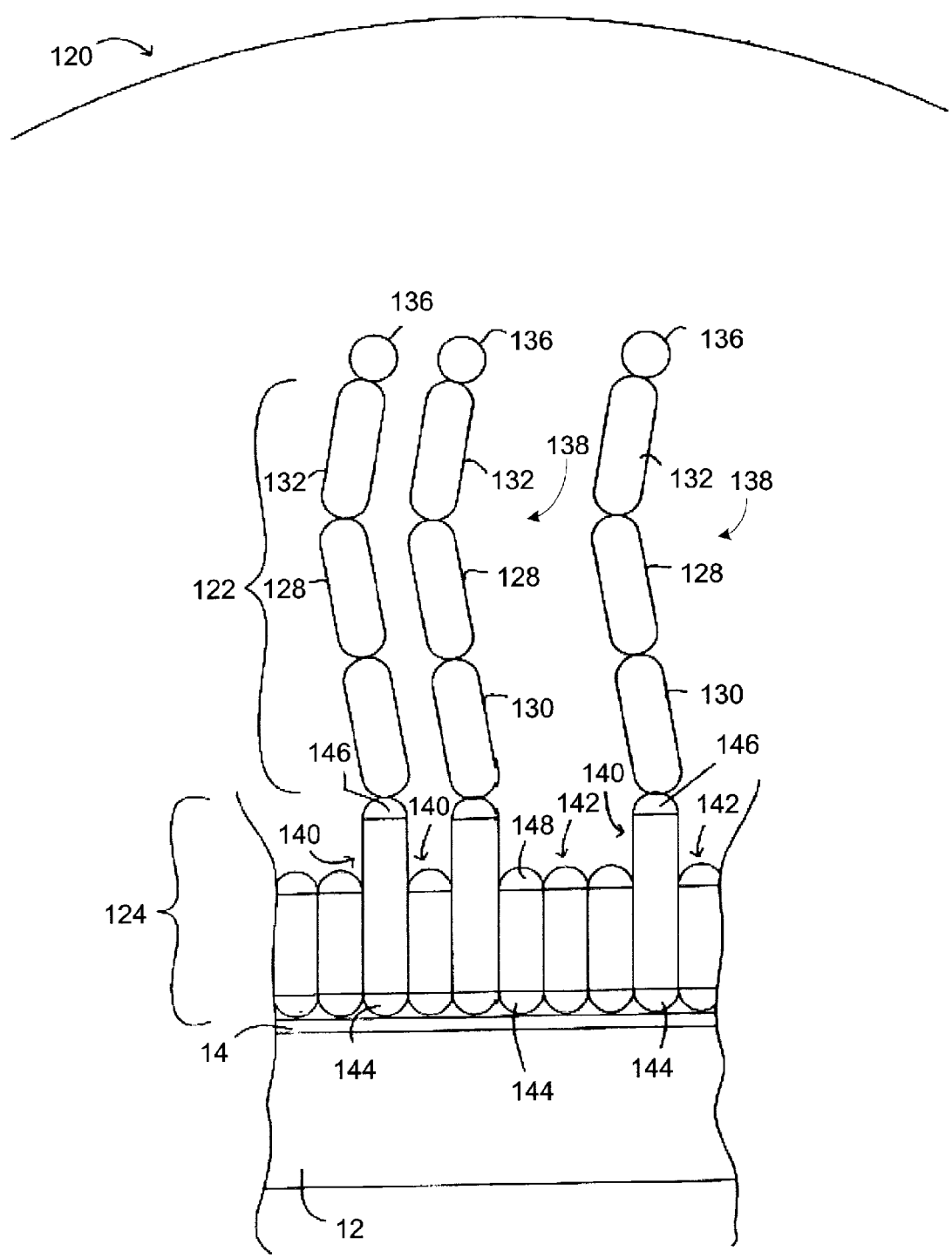
FIG. 9A illustrates an example of a test volume suitable for use with an electrochemical sensor.

As discussed above, when the sensors are electrochemical sensors, the sensors are prepared so as to include a test volume 120. FIG. 9A illustrates an example of a test volume 120 suitable for detection of polysaccharides, nucleic acids, cells, strands of genetic materials such as DNA or RNA and antibodies. The test volume 120 includes a test probe 122 bonded to the adhesion layer 124 on an electrode 14. A single test probe 122 is shown for the purposes of illustration; however, the density of the test probes 122 across the electrode 14 is generally much higher. The test probe 122 includes a portion of a target component 128 between a capture probe 130 and a signaling probe 132. The assay indicates the presence of the target component 128. Suitable target components 128 include, but are not limited to, polysaccharides, nucleic acids, cells and strands of genetic materials such as DNA or RNA and antibodies.

The adhesion layer 124 can increase the affinity of the capture probe 130 for the electrode 14 above the affinity the capture probe 130 has for the electrode 14 without the adhesion layer 124. The capture probe 130 serves to link the electrode 14 to the target component 128. As will become evident below, suitable capture probes 130 include, but are not limited to, deoxyribonucleic acids (DNA), ribonucleic acids (RNA), peptide nucleic acids (PNA), locked nucleic acids (LNA) and proteins such as antibodies.

A reporter 136 is bonded to the signaling probe 132. The signaling probe 132 is configured to link the target component 128 with the reporter 136. At least one mediator 138 is in the test volume 120. The mediator 138 and the reporter 136 can each exist in more than one state in the test volume 120. Examples of different states include different states of oxidation.

The illustrated adhesion layer 124 includes or consists of a self-assembly monolayer that has more affinity for the capture probe 130 than the electrode 14 has for the capture probe 130 when the self-assembly monolayer is not present on the electrode. A self-assembly monolayer is a two-dimensional film, one molecule thick, where each molecule is covalently bonded to a surface. The classical example of a self-assembly monolayer is the reaction of alkanethiols with a gold surface. Functionalized silane compounds can also self-assemble on silicon surfaces. Since molecules that are not bound directly to the surface can normally be washed away, self-assembly monolayers can provide a one molecule thick film immobilized on the surface.

The illustrated self-assembly monolayer is a heterogenous self-assembly monolayer that includes different compounds in the self-assembly monolayer. For instance, the illustrated self-assembly monolayer includes active probes 140 and spacers 142. The active probes 140 include an electrode linker 144. The electrode linker 144 is configured to link the active probes 140 to the electrode. The active probes 140 also include a probe linker 146. The probe linker 146 is configured to link the active probe 140 to the capture probe 130. For instance, the probe linker 146 can include one or more binding sites that are each configured to bind the capture probe 130. In some instances, the probe linker 146 is positioned at the terminal end of the active probes 140.

The spacers 142 each include an electrode linker 144 configured to link the spacers 142 to the electrode. The spacers 142 also include a terminal end 148. The terminal end 148 has less affinity for the capture probes 130 than the probe linker 146 has for the capture probes 130. In some instance, the terminal end 148 is configured such that the spacer 142 does not have substantial affinity for the capture probes 130. Accordingly, the capture probes 130 bond to the active probes 140 rather than the spacers 142.

The test volume 120 of FIG. 9A can also be adapted for detecting the presence of a cell or a protein. For instance, the capture probe 130 can be the primary antibody of a sandwich assay. Additionally, the signaling probe 132 can be the secondary antibody of the sandwich assay. Suitable target components 128 for a sandwich assay include, but are not limited to, proteins, polysaccharides and nucleic acids having binding sites specific to the antibody or cells with proteins having binding sites specific to the antibody.

Figure 9B:
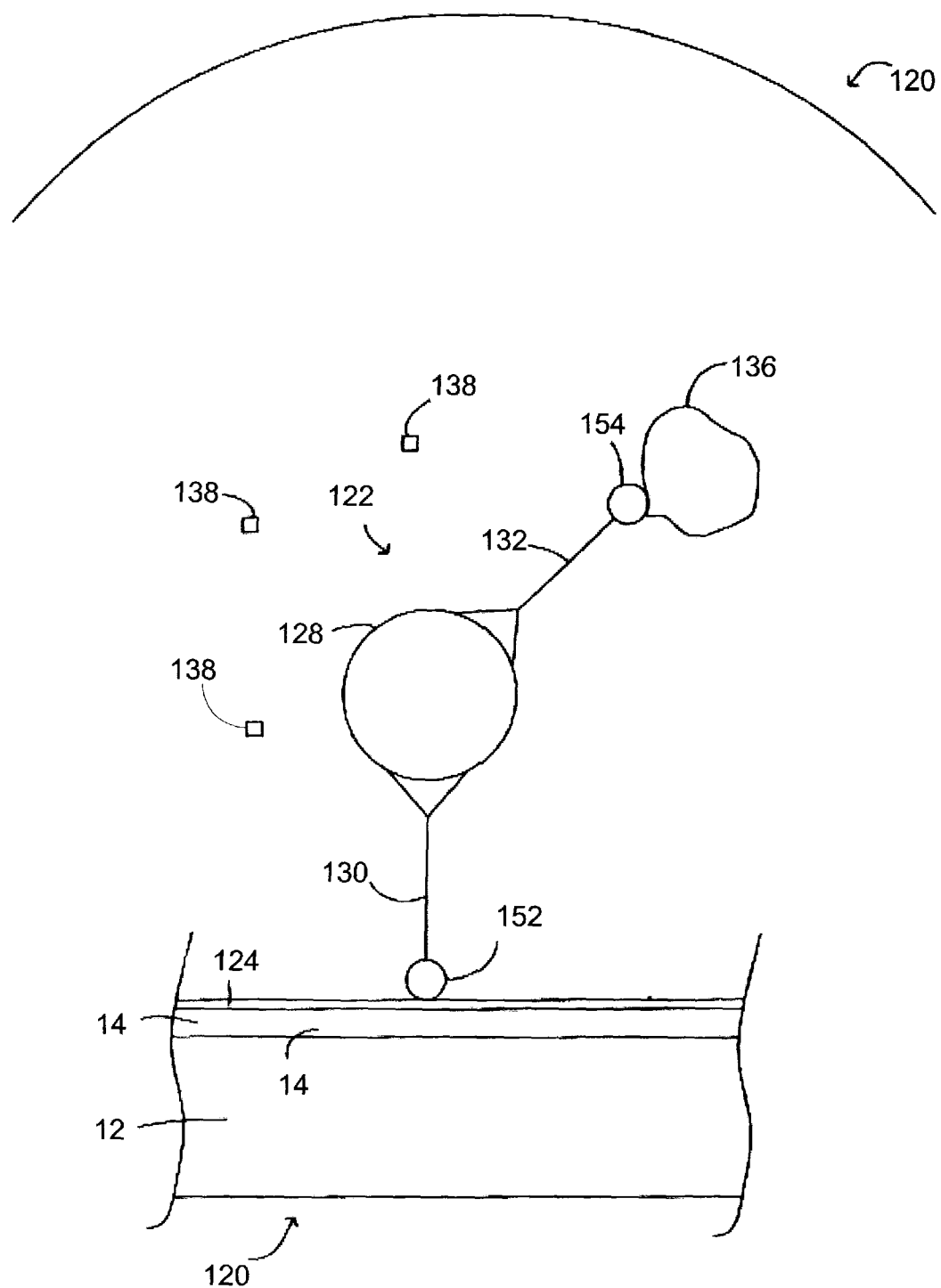
FIG. 9B illustrates another example of a test volume suitable for use with an electrochemical sensor.

A suitable reporter 136 for use with the assay components of FIG. 9B include, but is not limited to, Horseradish Peroxidase (HRP), AP (alkaline phosphotase) and glucose peroxidase. A suitable mediator 138 for use with HRP includes but is not limited to, 3,3',5,5'-tetramethylbenzidine (TMB). A suitable mediator 138 for use with AP includes but is not limited to, niacin derivative (NAD). A suitable mediator 138 for use with glucose peroxidase includes but is not limited to, ruthenium (II) hexamine.

The primary antibody can be modified to include a linker 152 that enhances bonding to the adhesion layer 124. For instance, when the adhesion layer 124 includes exposed streptavidin, the primary antibody can be modified with biotin that readily bonds with the streptavidin binding sites.

The secondary antibody can be modified to include a second linker 154 that enhances bonding to the reporter 136. For instance, when the reporter 136 includes HRP, the secondary antibody can be modified to encourage bonding of the signaling probe 132 to the HRP. For instance, the secondary antibody can be modified with fluorescein that can serve as a linker to the HRP.

In some instances, the capture probe 130 is modified with a linker that enhances bonding of the capture probe 130 to the adhesion layer 124. For instance, when the self-assembly monolayer includes streptavidin, the capture probe 130 can be modified with biotin that readily bonds with streptavidin binding sites.

Example 1

In one example, a test volume for testing for the amount and/or presence of protein marker in blood is formed by injecting the blood into an inlet port 46 using a fluid conduit such as a needle 48. A system such as the system of FIG. 6A is then employed to inject a series of reagents into another inlet port 46 through an output conduit 76. The series of reagents can include 0.5 ml of a blood sample wash such as DI water followed by 0.1 ml of an enzyme such as HRP, followed by 0.5 ml of an enzyme wash such as Tween, followed by 0.1 ml of 3,3',5,5'-tetramethylbenzidine (TMB), followed by 1 ml of a dummy solution or purging volume such as DI water. Electrochemical testing can be performed on the resulting test volume.

Other embodiments, combinations and modifications of this invention will occur readily to those of ordinary skill in the art in view of these teachings. Therefore, this invention is to be limited only by the following claims, which include all such embodiments and modifications when viewed in conjunction with the above specification and accompanying drawings.

The invention claimed is:

1. A system, comprising:
a cartridge including a sensor structure, the sensor structure including multiple sensors positioned on a substrate,
the sensors are each an electrochemical sensor that includes a working electrode, a counter electrode, and a reference electrode;
a common channel defined in the cartridge such that a fluid flowing in the common channel contacts each of the sensors as a result of the fluid flowing from an inlet of the common channel to an outlet of the common channel, and
the common channel does not branch into other channels between the inlet and the outlet.

2. The system of claim 1, further comprising:
a selection valve in liquid communication with reagents that are each in a different container, the selection valve being in liquid communication with the common channel, the selection valve configured to select any one of the reagents for transport into the common channel.

3. The system of claim 2, wherein the selection valve selects one of the reagents for transport into the common channel by opening liquid communication between the common channel and the container that contains the selected reagent and closing liquid communication between the common channel and each of the containers that contains an unselected reagent.

4. The system of claim 3, further comprising:
a pump configured to pump the selected reagent from the container that contains the selected reagent.

5. A method, comprising:
overlapping substrates with one another such that more than one of the substrates each has an overlapped portion that is overlapped by one or more of the other substrates and also has an exposed portion that is not overlapped by any of the other substrates; and
forming electrodes on the substrates while they are overlapped, the electrodes being formed on the exposed portions of different substrates.

6. The method of claim 5, further comprising:
assembling a cartridge that includes a first one of the substrates and the electrodes formed on the first substrate,
the cartridge including one or more channels arranged such that a liquid in the channel contacts the electrodes on the first substrate.

7. The method of claim 6, further comprising:
employing more than one of the sensors to perform cyclic voltammetry.

8. The method of claim 5, wherein the electrodes are the electrodes of an electrochemical sensor.

9. The method of claim 5, wherein forming the electrodes includes sputtering through a mask.

10. The method of claim 5, wherein one or more of the substrates that each has one of the exposed regions has the exposed region occupying more than 25% of the total area of an upper surface of the substrate, the overlapped regions of the one or more substrates occupying more than 25% of the total area of an upper surface of the substrate, and a perimeter of the edge of each of the one or more substrates being aligned with more than 25% of a perimeter of an edge of another one of the substrates.

11. The method of claim 10, wherein one or more alignment structures limit movement of the overlapped substrates during the formation of the electrodes.

12. A system, comprising:

substrates overlapped with one another such that more than one of the substrates each has an overlapped portion that is overlapped by one or more of the other substrates and also has an exposed portion that is not overlapped by any of the other substrates; and electrodes on the exposed portions of different substrates.

13. The system of claim 12, wherein the electrodes on are arranged so as to define multiple electrochemical sensors on different substrates.

14. The system of claim 13, wherein one or more of the substrates that each has an exposed region has an exposed region that occupies more than 25% of the total area of an upper surface of the substrate, the one or more substrates each has an overlapped region that occupies more than 25% of the total area of an upper surface of the substrate, and a perimeter of the edge of each of the one or more substrates is aligned with more than 25% of a perimeter of an edge of another one of the substrates.

15. A system, comprising:

a cartridge including a sensor structure, the sensor structure including multiple sensors positioned on a substrate, the sensors each includes multiple electrodes and capture probes are bonded to one or more electrodes in each of the sensors, the capture probes being configured to bond directly to a target component during operation of the sensors, and a first portion of the sensors having the one or more electrodes bonded to different capture probes than the capture probes that are bonded to the one or more electrodes in a second portion of the sensors;

a common channel defined in the cartridge such that a fluid flowing in the common channel contacts each of the sensors as a result of the fluid flowing from an inlet of the common channel to an outlet of the common channel, and the common channel does not branch into other channels between the inlet and the outlet.

16. The system of claim 15, wherein the electrodes in each sensor includes a working electrode, a counter electrode, and a reference electrode.

17. The system of claim 15, further comprising:

a selection valve in liquid communication with reagents that are each in a different container, the selection valve being in liquid communication with the common channel, the selection valve configured to select any one of the reagents for transport into the common channel.

18. The system of claim 17, wherein the selection valve selects one of the reagents for transport into the common channel by opening liquid communication between the common channel and the container that contains the selected reagent and closing liquid communication between the common channel and each of the containers that contains an unselected reagent.

19. The system of claim 18, further comprising:

a pump configured to pump the selected reagent from the container that contains the selected reagent.

* * * * *